United States Patent [19]

Mast et al.

[11] 4,240,287

[45] Dec. 23, 1980

[54] SAND DETECTION

[75] Inventors: Harm Mast; Jan W. Kraayeveld; Peter B. Vriezen; Gerrit J. Wunnink, all of Rijswijk, Netherlands

[73] Assignee: Shell Oil Company, Houston, Tex.

[21] Appl. No.: 957,265

[22] Filed: Nov. 2, 1978

[30] Foreign Application Priority Data

Dec. 20, 1977 [GB] United Kingdom ............... 52958/77

[51] Int. Cl.³ ............................................. G01N 15/07
[52] U.S. Cl. ....................................... 73/61 R; 73/155
[58] Field of Search .................. 73/432 PS, 28, 61 R, 73/155; 235/92 MT, 92 AE, 92 FL, 92 PK

[56] References Cited

U.S. PATENT DOCUMENTS

| | | | |
|---|---|---|---|
| 2,760,184 | 8/1956 | Beattie | 73/194 A X |
| 3,271,672 | 9/1966 | Henderson | 235/92 FI X |
| 3,563,311 | 2/1971 | Stein | 73/155 X |
| 3,834,227 | 9/1974 | Patterson et al. | 73/155 |
| 3,841,144 | 10/1974 | Baldwin | 73/61 R |
| 3,844,174 | 10/1974 | Chabre | 73/432 PS |
| 3,854,323 | 12/1974 | Hearn et al. | 73/61 R |
| 3,989,965 | 11/1976 | Smith et al. | 310/334 |
| 4,016,766 | 4/1977 | Morris | 235/92 AE X |
| 4,065,960 | 1/1978 | Grabendörfer | 73/609 |
| 4,131,815 | 12/1978 | Boatright | 310/323 |

Primary Examiner—Daniel M. Yasich

[57] ABSTRACT

A method and apparatus for detecting sand particles in a flowing fluid, for example, the production from a gas or oil well. An acoustic transducer is used to detect the sand particles and the resulting signal is filtered to pass a frequency band of 50 to 500 kiloherz. A pulse height discriminating means and pulse counter is provided for counting the number of pulses that exceed a pre-set amplitude.

9 Claims, 6 Drawing Figures

U.S. Patent
Dec. 23, 1980
4,240,287
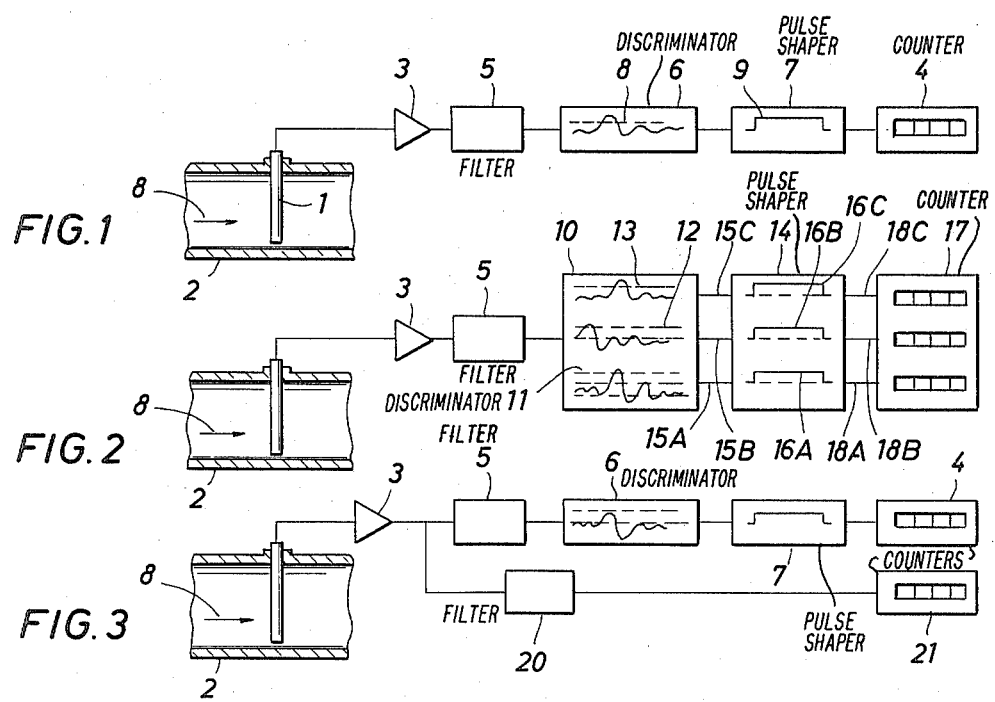
FIG.1
FIG.2
FIG.3
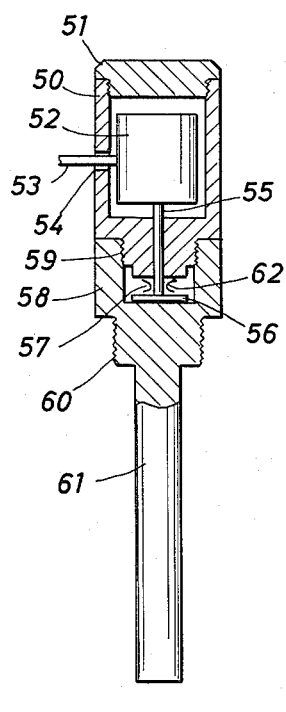
FIG.4
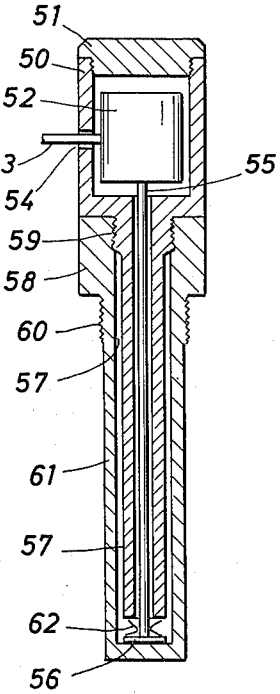
FIG.5
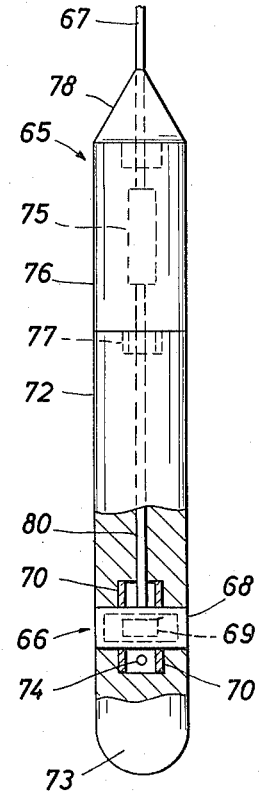
FIG.6

SAND DETECTION

BACKGROUND OF THE INVENTION

The invention relates to a method and means of detecting solid particles in a fluid flowing through a conduit.

The invention relates in particular to a method and means for counting the number of particles that pass through a pre-determined area of the cross-section of the conduit and for counting the particles and optionally differentiating in the size of the particles when these are of one and the same composition.

Solid particles, such as sand grains, are often entrained in a flowing fluid that is being recovered from an underground formation, such a formation containing hydrocarbons. The sand grains entrained with the fluid (such as gas and/or liquid hydrocarbons) can cause erosion of the conduits in the well, as well as the pipelines and fluid treating installations on the surface. In order to take timely counter-measures, an early warning is required of the presence of those amounts of sand grains that can be expected to cause damage of the recovery equipment in the well or on the production site.

A method and equipment for detecting solid particles in a flowing fluid is known already, wherein at least part of the particles carried by the flowing fluid impinges against a microphonic probe. Each impact is recorded separately, since the impacts are distinguishable from background noise. Also, a method and apparatus for grain detection in a flowing fluid is described in U.S. Pat. Nos. 3,816,773; 3,841,144; 3,854,323 and 3,908,454 in which the grains activate transducer means responsive to acoustic energy to generate a signal representative of said energy, wherein a frequency range around 700 kHz of the signal is held to be representative of the kinetic energy of the total amount of grains striking the transducer means and a frequency range around 100 kHz of the signal is held to be representative of the background noise.

Further, a method and means are known for detecting individual solid particles that are being carried in a particular flow area of a flowing fluid. Herein, the grains impinge on a piezoelectric transducer. The peak value of the resulting electric output signal is detected in a pulse height discriminator after a suitable amplification of this signal. When the peak value exceeds a preset discrimination level, a standard output pulse is produced with a length that is greater than the typical duration of the impact signal. The number of standard pulses is counted in a pre-determined period. At a given velocity, the grain diameter can be estimated from the peak amplitude of the impact response, and a differentiation can be made between different ranges of grain sizes which will lead to a grain-size distribution of the grains that pass through a given area of the cross-section of the conduit over a given period.

BRIEF SUMMARY OF THE INVENTION

It has now been found that best results will be obtained by the above method wherein counts are made of the number of grains impinging on a transducer element, when the transducer signal is selectively filtered.

According to the invention, a method of detecting solid particles in a fluid flowing through a conduit comprises the steps of generating an electric signal by allowing particles to impinge against an acoustic transducer means, filtering said signal to pass frequency components thereof in a range that is within the frequency band of about 50 kHz to about 500 kHz, comparing the values of the amplitudes of each pulse train in the filtered signal with at least one pre-determined range of values, creating an electric standard pulse when the maximum amplitude of such pulse train has a value that is within said pre-determined range, and counting the number of standard pulses over a pre-determined period.

The electric signals are preferably generated by a piezoelectric element that is activated by the particles through the intermediary of a metal body.

According to the invention, a means of detecting solid particles in a fluid flowing through a conduit comprises acoustic transducer means adapted to be positioned in a conduit through which a particle-laden fluid may pass. A circuit means connects the transducer to a means for indicating the number of impacts made by particles on the acoustic transducer means. The circuit means comprising filter means for processing the electric signals generated by the transducer means to pass frequency components thereof in a range that is within the frequency band of about 50 kiloherz to 500 kiloherz, and a pulse height discriminating means and a pulse shaper means. The circuit means and pulse height discriminating means are adapted to form a standard pulse to be passed on to the indicating means each time the value of the maximum amplitude of a pulse train in the filtered signal is within a range of pre-determined values.

The transducer means preferably comprise a piezoelectric element that is in contact with a metal body, which body is adapted to be arranged in the conduit to be exposed to the flow of fluid.

BRIEF DESCRIPTION OF THE DRAWINGS

The invention will now be described by way of example in more detail with reference to the drawing. In the drawing, FIG. 1 shows schematically an acoustic transducer means positioned in a conduit and a block diagram of the electric means used for processing and counting the signals generated by the transducer means;

FIG. 2 shows schematically the particle detecting system according to FIG. 1 but now equipped for differentiating between various particle sizes;

FIG. 3 shows schematically the particle detecting system of FIG. 1 in combination with means for detecting fluid flow velocity;

FIG. 4 shows a longitudinal section over a transducer means to be used in any one of the systems of FIGS. 1–3;

FIG. 5 shows a longitudinal section of an alternative of the transducer means of FIG. 4; and FIG. 6 shows an acoustic transducer means that can be used as acoustic transducer means in any one of the systems shown in FIGS. 1–3 and is adapted to be displaced vertically in a well for discriminating between the particles that enter the well at various levels.

The particle detecting system according to FIG. 1 comprises an acoustic transducer means 1 arranged in a conduit 2. The transducer means comprise a piezo-electric element (not shown) that is arranged in the transducer means 1 such that any particle impinging against the outer wall of the means 1 generates an electric signal in the form of a pulse train. This signal is subsequently supplied to the amplifier 3, which amplifier 3 is part of a circuitry system that feeds signals to the counting and display means 4. Apart from the amplifier 3 and connecting wires, the circuitry system comprises a frequency filter 5, a pulse height discriminator 6, and a pulse shaper 7.

The signals amplified by the amplifier 3 are filtered by the frequency filter 5 to pass only those components of the amplified signal that have a frequency between 100 kiloherz and 300 kiloherz. The filtered signals are subsequently supplied to the pulse height discriminator 6 where the values of the amplitudes of each pulse train in the filtered signal are compared with the pre-determined range of values above level 8. Each pulse having an amplitude above the predetermined level 8 generates a signal that is passed to the pulse shaper 7 which in its turn generates a standard pulse 9 that is supplied to the means 4, which counts and displays the number of standard pulses supplied thereto during a pre-determined period.

The length of the standard pulse 9 produced by a particle impact signal with a maximum amplitude of value that is within the range of values above level 8, may be 200 $\mu$sec. During these 200 $\mu$s time intervals no new standard pulses can be triggered. This prevents secondary peaks of the same impact signal from triggering new output pulses. Two particle impacts within 200 $\mu$s will then be counted as one impact, but this has been found to raise a small error only which is negligible for the purpose of which the particle detecting system is designed.

It will be appreciated that the height of the level 8 in the pulse height discriminator 6, as well as the length of the standard pulse may be made adjustable to allow the operator to select an optimum value for the operating conditions.

It has been found that the best results are obtained by the particle detection system designed for counting the number of particles impinging against the acoustic transducer means, if the signal generated by the transducer means is filtered to pass frequency components thereof in a range that is within the 50 kHz–500 kHz band. This will be in particular the case when applying acoustic transducer means 1 comprising a piezo-electric element that is in contact with a metal body against which the particles impinge. Such acoustic transducer means will be described in more detail hereinafter with reference to FIGS. 4 and 5 of the drawing.

The particle detecting system shown in FIG. 2 differs from the system shown in FIG. 1 in that it comprises a pulse height discriminator 10 that is designed to differentiate between various ranges of pulse heights. The signals generated by particles impinging upon the acoustic transducer 1 arranged in the conduit 2 are first supplied to amplifier 3 and subsequently to the filter 5 wherein the frequencies outside the range of 50 kHz–200 kHz are suppressed. The resulting pulse trains are then supplied to the pulse height discriminator 10, that can differentiate between the maximum amplitudes of the pulses that are either above the level 11, or between the levels 11 and 12, or between the levels 12 and 13.

A particle impact that generates a pulse train whereof the value of the maximum aplitude is within the range of values above the level 11, will then be passed on to the pulse shaper 14 through the electric connection 15A. The pulse shaper 14 generates a standard pulse 16A that is subsequently passed to the counting and display means 17 via the electric connection 18A. Thus all impacts on the transducer means 1, which generate a pulse train with maximum amplitude above level 11 will be separately counted by counter 17 and separately displayed thereby.

Further, all impacts that generate a pulse train with maximum amplitude in the range of values between the levels 11 and 12 will also be separately counted and displayed by the counter 17. The same applies for the impacts that generate a pulse with a maxiumum amplitude that has a value falling within the range of values between the levels 12 and 13.

It will be appreciated that the discriminator 10 and the pulse shaper 14 are designed such that the detection of a maximum value of the amplitude of the pulse train that is within one of the pre-determined ranges of values only allows the formation of a single standard pulse to be passed on to the display means 17. Triggering of standard pulses that correspond with secondary peaks of the same pulse train may be prevented by giving the standard pulse a length that exceeds the length of the pulse trains. Each impact is counted only in that one of the three displays of means 17 that corresponds to the range reached by the maxiumum amplitude of the pulse train. Such is established by blocking during the counting period the passage through those two of the electric connections 15A–C (or of the connections 18A–C) that lead to the other two displays of the means 17. Electric circuits for such purpose are known per se and do not require a detailed description.

The levels 11, 12 and 13 may be made adjustable. The system is calibrated for a certain range of masses of the solid particles that are entrained with the fluid flow 8, and for a certain rate of this flow. The display of the counting means 17 will—over a pre-determined time interval—indicate the total amount of particles that have passed through a particular area of the cross-section of the conduit 2, as well as the distribution of these particles according to three size-ranges.

The flow rate of the fluid may be detected by the system of the present invention in the embodiment thereof that is shown in FIG. 3. This system is similar to the system shown in FIG. 1, but has added thereto an electric filter 20 that is designed to suppress all frequencies outside the 50–10,000 Hz range. The signals generated by the transducer means 1 are supplied to this filter 20 after being amplified by the amplifier 3, and the filtered signal that substantially originates from the background noise in the conduit is representative of the rate of the fluid flow 8 through the conduit 2. The magnitude of the signal in the frequency range of 50–10,000 Hz is indicated by the display 21.

It is particularly advantageous to use a filter similar to the filter 20 in combination with the particle detecting system shown in FIG. 2, since the output signal of the filter may then be used for adjusting the levels 11, 12 and 13 of the pulse height discriminator 10 such that the counter 17 always indicates the number of particles in three fixed size ranges independent of the magnitude of the flow rate of the fluid 8 passing through the conduit 2.

FIGS. 4 and 5 of the drawing show acoustic transducer means for use in the systems shown in FIGS. 1–3. Each transducer means comprises a housing 50 with cover 51, which housing houses a pre-amplifier 52. The output cable 53 of the amplifier passes through an opening 54 in the wall of the housing 50, and the input cable 55 is electrically connected to the piezo-electric crystal 56 that is arranged in the interior 57 of extension 58 of the housing 50. The extension 58 is connected to the housing 50 by means of a screw thread 59.

The outer wall of the extension 58 carries a screw thread 60, for connecting the acoustic transducer means to the conduit (not shown) wherein the measurement should take place. Screw thread 60 is designed for cooperation with a screw threaded opening in the wall of such conduit, such that the part 61 of extension 58 of housing 50 is within this conduit in the operative position of the transducer means.

A spring element 62 is arranged within the interior 57 of the extension 58, this spring element pressing one side of the piezo-electric crystal 56 against the bottom wall of the interior 57 of the extension 58. The extension 58 is made of metal (such as copper) and acoustic waves generated by impact of particles on the outside wall of extension 58 are consequently transmitted to the piezo-electric crystal 56 and detected thereby.

The means for detecting solid particles in a fluid flowing through a conduit as shown in FIGS. 1-3 of the drawing are designed for detecting these particles in a fluid flowing through a conduit wherein the acoustic transducer element can be easily mounted in the conduit. Such conduit may be a conduit leading from a well producing gaseous hydrocarbons to a treating installation. The presence of solid particles in the fluid, such as gas that flows out of the well, is then detected and a warning may be given to the operator in case the amount of solid particles surpasses an undesired level.

However, the present invention may also be used for detecting the presence of solid particles in the well itself. An acoustic transducer element is then supported by a small diameter cable in which electric wires are incorporated for passing signals from the transducer element to the surface. The transducer element is then lowered by the cable to a desired level in the well and the signals generated by the impacts of solid particles against the transducer element thereof are passed to the surface via the electric wires. Preferably, the signals are amplified prior to passing them to the surface. If desired, suitable carrier waves (such as F.M. waves) may be used for transmitting these data from the transducer element to the surface.

FIG. 6 shows a logging tool 65 comprising a transducer element 66, which logging tool is supported by a cable 67. This tool is in particular designed for detecting the level at which solid particles are entering a well together with hydrocarbon or other gases that enter the well via perforations in the casing that lines the well to prevent collapse thereof.

Such perforations consist of small diameter openings in the wall of the casing and depending on the degree of consolidation of the formation layers facing the perforations and the rate at which the gas flows out of the various formation layers, sand particles will be entrained with the gas entering the well. It may be found desirable to detect the level of the perforation or perforations through which sand particles are entering the well, and the logging tool shown in FIG. 6 has been found to be useful for this purpose.

The logging tool 65 of FIG. 6 comprises a housing 68 wherein a piezo-electric crystal 69 is supported in acoustic contact with the wall of the housing. This housing consists of metal or other acoustic wave transmitting material and comprises external extensions 70 that connect the housing 68 to acoustic barrier elements 72 and 73. These acoustic barrier elements are made of suitable material, such as a resinous material incorporating heavy particles, such as metal particles (e.g., lead shot). Openings 74 may be provided in the walls of the extensions 70 to obtain a strong connection between the housing 68 and the material of the barriers 72 and 73, which are preferably formed in-situ on the housing 68.

Electric signals are generated by the transducer element 69 by sand particles travelling in a direction substantially at right angle to the central axis of the logging tool 65 and impinging against the outer wall of the housing 68 thereof. By passing the oblong logging tool 65 through the perforated casing in a well, any particle that enters the well via a perforation, will generate a signal in the transducer element 69, which signal is passed on via electric cable 80 to an amplifier 75 carried in the housing 76 situated above the acoustic barrier 72 and connected thereto by means of an extension 77. The amplified signal is then passed on to the surface via the support cable 67 that has electric cables for data transmission incorporated therein. The cable 76 is connected to the logging tool by means of the screw cap 78.

Since the length of the cable 67 that supports the logging tool 65 in a well can be measured, the level at which electric signals are obtained by the impact of sand particles against the side wall of the housing 68 can easily be calculated. This level indicates the level at which the sand particles are entering the well and after removal of the logging tool corrective measures can be taken to consolidate the formation layer facing the perforation(s) at that particular level. Such consolidation treatments are known per se and do not form part of the present invention.

The cable 67 is at the surface connected to one of the electric circuits shown in FIGS. 1-3, which allows the operator to obtain information on the amount of sand grains that enter the well at the level at which the housing 68 of the tool 65 is situated.

The transducer element 69 further generates signals that originate from sand particles that impinge against the acoustic barrier elements 72 and 73, as well as from sand particles that travel in directions parallel to the longitudinal axis of the logging tool 65. These signals, however, have relatively low amplitudes, and by adjusting the lowest discrimination level in the discriminator 6 (see FIGS. 1-3) above said relatively low amplitudes, the impacts represented by these signals will not be counted by the means 4 and 17. Thus, the impacts counted by the means 4 and 17 are representative only of the impacts of those sand grains that have hit the side wall of the housing 68.

It will be appreciated that apart from the piezo-electric crystals that have been indicated hereinabove as being suitable for use as an acoustic transducer in the present invention, other types of acoustic transducer may be applied with the same favorable results.

Application of the invention is not restricted to the use of the bandpass filters 5 as described with reference to FIGS. 1 and 2 having frequency ranges of 100 kHz–300 kHz and 50 kHz–200 kHz, respectively. Any other filter may be applied that is designed to pass those signal components that have a frequency within a frequency range other than the two ranges referred to above, but having a lower boundary that is above about 50 kHz and an upper boundary that is below about 500 kHz.

The filtering action to remove the high frequencies from the signals may either be performed by a specially designed filter, or take place in the transmission lines.

What we claim is:

1. A method of detecting solid sand particles in a fluid flowing from a well through a conduit, comprising:

an acoustic transducer means having a housing with a piezoelectric element disposed therein, said piezoelectric element being biased into contact with one wall of said housing, said piezoelectric element in addition being coupled to a preamplifier disposed in said housing;

generating an electric signal by allowing the particles to impinge against the housing of said acoustic transducer means;

filtering said signal to pass frequency components thereof in a pulse train ranging within the frequency band of about 50 kHz to about 500 kHz;

comparing the values of the amplitudes of each said pulse train in the filtered signal with at least one predetermined range of amplitude values;

generating for each pulse train an electric standard pulse having a predetermined time period and amplitude when the maximum amplitude of said pulse train has a value that is above said one of predetermined range of amplitude values; and, counting the number of standard pulses generated by said pulse train within each set predetermined period.

2. The method according to claim 1, wherein the signal generated by the acoustic transducer means apart from being filtered in a range within the frequency band of about 50 kHz to about 500 kHz, is separately filtered to pass frequency components thereof in the range of about 100 herz to about 10,000 herz, which latter filtered signal is representative of the flow rate of the fluid.

3. The method according to claim 1, wherein the acoustic transducer means are suspended in a well penetrating a subsurface formation.

4. Means for detecting solid sand particles in a fluid flowing from a well through a conduit, comprising:

an acoustic transducer means having a housing with a piezoelectric element disposed therein, said piezoelectric element being biased into contact with one wall of said housing, said piesoelectric element in addition being coupled to a preamplifier disposed in said housing;

indicating means for indicating the number of impacts made by particles on the acoustic transducer means; and, circuitry means interconnecting said transducer means and said indicating means, said circuitry means comprising filter means for processing the electric signals generated by the transducer means to pass frequency components thereof in a pulse train ranging within the frequency band of about 50 kHz to about 500 kHz, a pulse height discriminating means and a pulse shaper means, said two latter means being adapted to form for each pulse train a standard pulse having a predetermined time period and amplitude, said standard pulse being passed on to the indicating means each time the value of the maximum amplitude of a pulse train is above a preset range of values in the filtered signal.

5. Means according to claim 4, wherein the predetermined time period of said standard pulse is variable.

6. Means according to claim 4 or 5, including further circuitry means comprising filter means for processing the electric signals generated by the transducer means to produce signals in the frequency range of about 100 herz to about 10,000 herz.

7. Means according to claim 6, comprising display means for displaying the signals in the frequency range of about 100 herz to about 10,000 herz.

8. Means according to claim 4, wherein the transducer means are adapted to be suspended by cable means for vertically displacing said transducer means in a well.

9. Means according to claim 8, wherein the acoustic transducer means comprise a cylindrical housing arranged between two acoustic barrier elements, the housing and the barrier elements together forming an oblong logging tool.

* * * * *